United States Patent [19]
Gupta

[11] Patent Number: 5,698,854
[45] Date of Patent: Dec. 16, 1997

[54] METHOD AND APPARATUS FOR INSPECTING PIPES

[75] Inventor: Nand K. Gupta, Libertyville, Ill.

[73] Assignee: Omega International Technology, Inc., Lakemoor, Ill.

[21] Appl. No.: 650,533

[22] Filed: May 20, 1996

[51] Int. Cl.⁶ .................................................. G01N 23/18
[52] U.S. Cl. ........................................ 250/358; 250/360.1
[58] Field of Search .............................. 250/358.1, 359.1, 250/360.1, 308, 253

[56] References Cited

U.S. PATENT DOCUMENTS

| | | |
|---|---|---|
| 2,957,987 | 10/1960 | Arnesen . |
| 3,109,095 | 10/1963 | Van Horne ..................... 250/358.1 X |
| 3,178,576 | 4/1965 | Arvanetakis . |
| 3,686,932 | 8/1972 | Ries et al. . |
| 3,702,934 | 11/1972 | Jakobsen . |
| 3,775,612 | 11/1973 | Foster et al. . |
| 3,835,323 | 9/1974 | Kahil . |
| 3,835,324 | 9/1974 | Weigle . |
| 4,064,440 | 12/1977 | Roder . |
| 4,146,791 | 3/1979 | Dahl et al. . |
| 4,150,289 | 4/1979 | Rossauer et al. . |
| 4,187,425 | 2/1980 | Thompson . |
| 4,415,980 | 11/1983 | Buchanan . |
| 4,495,635 | 1/1985 | Dobbs ............................. 250/359.1 X |
| 4,695,729 | 9/1987 | Monno et al. . |
| 4,725,963 | 2/1988 | Taylor et al. . |
| 4,870,669 | 9/1989 | Anghaie et al. . |
| 4,947,045 | 8/1990 | Birks et al. . |
| 5,138,644 | 8/1992 | McArdle et al. . |
| 5,268,952 | 12/1993 | Tarvainen . |
| 5,371,363 | 12/1994 | Lilimpakis . |
| 5,388,136 | 2/1995 | Halliday et al. . |
| 5,414,648 | 5/1995 | Morgan et al. ..................... 250/359.1 X |
| 5,420,427 | 5/1995 | Morgan et al. . |

*Primary Examiner*—Edward J. Glick
*Attorney, Agent, or Firm*—Brinks Hofer Gilson & Lione

[57] ABSTRACT

An apparatus adapted for inspecting and measuring the wall thickness of a length of pipe. The apparatus includes a carriage adapted to be movably mounted along the length of pipe, a source emitting a beam of penetrating energy and a detector array having a plurality of detectors arranged in an elongated array. The array receives and measures the intensity of the energy beam. The detector array is mounted on the carriage in a spaced apart relationship with the source so as to allow the diameter of the pipe to pass between them. The detector array is oriented so that its length is positioned generally perpendicular to the intended path of travel. A method is also provided for inspecting and measuring the wall thickness of the pipe. The method includes the steps of providing a length of pipe and an apparatus that includes a source of penetrating energy and a elongated detector array mounted on a carriage. The method also includes positioning the apparatus on the pipe so that the diameter of the pipe is disposed between the array and the source, and propelling the apparatus along the axial direction of the pipe while receiving and measuring the intensity of the energy beam received by the detector array.

45 Claims, 7 Drawing Sheets

METHOD AND APPARATUS FOR INSPECTING PIPES

BACKGROUND OF THE INVENTION

The present invention relates generally to a measuring device and method, and in particular, to a device and method for measuring the wall thickness of a length of pipe.

Pipelines are an integral part of industry, and are widely used in refineries, power plants and other industrial applications. Pipelines, particularly pipelines used in these applications, deteriorate over time, causing a thinning of the pipe walls. Thinning of pipe walls in these applications commonly is caused by flow assisted corrosion or erosion. In addition, moisture, such as from rain and snow, can be trapped between insulation placed around the periphery of the pipe and the outer surface of the pipe. The trapped moisture can corrode the pipe under the insulation, thereby causing a thinning of the pipe walls. Thinning of the pipe walls can make the pipeline susceptible to rupturing, particularly when pressurized. Failure of the pipe wall, and the resultant leakage, can lead to facility downtime, require expensive repairs, and cause serious injury to workers and the environment.

Because flow-assisted corrosion and erosion, and corrosion under insulation, cannot be detected by visual inspection, various methods and devices have been developed for non-destructive inspection of pipelines. For example, it is common in the industry to use ultrasonic methods for evaluating the wall thickness of the pipe. However, this method cannot be used on insulated pipes unless the insulation is removed at each point of inspection, which can be expensive and time consuming. Moreover, the thickness is measured at discrete intervals along the length of the pipe and at intervals around the periphery of the pipe, rather than on a continuous basis.

Alternatively, U.S. Pat. No. 5,138,644, entitled METHOD AND APPARATUS FOR MEASURING THE WALL THICKNESS OF INSULATED PIPE, discloses a method and apparatus for measuring the thickness of a pipe without the insulation being removed. However, the apparatus only measures the thickness of the pipe at a particular cross-section along its length. Accordingly, as with the ultrasonic methods, the device can only be used to take measurements at discrete, predetermined locations or intervals. This can be extremely time consuming and expensive.

U.S. Pat. No. 5,268,952, entitled MEASURING APPARATUS FOR MEASURING FAULTS IN A PIPELINE, discloses an apparatus that moves along the axial direction of the pipe while emitting collineated beams of gamma or x-ray radiation that are received by two detectors placed one after the other along the axial direction of the pipe. The detectors measure the intensity of the beams as they pass through the pipe. Thinning of the walls or the presence of obstructions can be detected by measuring a change in intensity of the beam received at the detectors. However, the detectors only measure intensity differences along a very narrow, discrete path defined by the width of the detectors, which are aligned along the length of the pipe. Thus, the system is incapable of evaluating the entire width of the pipe in a single pass. Moreover, the system only displays the intensity of the beams measured by the pair of aligned detectors and is therefore incapable of providing a radiographic image of the pipe wall.

SUMMARY OF THE INVENTION

Briefly, the present invention is directed to an apparatus adapted for inspecting and measuring the wall thickness of a length of pipe. The apparatus includes a carriage which is adapted to be movably mounted on the length of the pipe, a source emitting a beam of penetrating energy and a detector array. The detector array includes a plurality of detectors arranged in an elongated array which is oriented so that its length is positioned generally perpendicular to the intended path of travel of the carriage along the length of pipe. The plurality of detectors receive and measure the intensity of the beam of energy emitted by the source. In this way, the apparatus can measure and record the wall thickness of the pipe, which is directly related to the intensity of the beam measured by the detectors, in a single pass as it is moved along its length.

In one aspect of the invention, the apparatus also includes a computer which is adapted to receive and store output from the detectors in the array as they measure the intensity of the beam. The computer is adapted to receive an analog signal from the detector and convert it to a digital signal. In a preferred embodiment, the computer is programmed to provide notice to a user, such as by marking the pipe, when the computed wall thickness falls below a predetermined minimum value.

In another aspect of the invention, the carriage is adapted to be self propelled. In a preferred embodiment, the propulsion is remote-controlled.

In yet another aspect of the invention, a method is provided for inspecting and measuring the wall thickness of the pipe. The method includes the steps of providing an apparatus that includes a carriage, an energy source and a detector array. The apparatus is propelled along the axial length of the pipe, whose diameter is disposed between the source and detector array. The source emits a beam of penetrating energy which is received by the detector array. The intensity of the beam received by each detector is collected and used to calculate the thickness of the pipe wall.

The present invention, together with further objects and advantages, will be best understood by reference to the following detailed description taken in conjunction with the accompanying drawings.

DETAILED DESCRIPTION OF THE PREFERRED EMBODIMENTS

Referring to the drawings, FIGS. 3–6 show an embodiment of an apparatus 2 for measuring the wall thickness of a length of pipe 50. The apparatus 2 includes a carriage 12, a source 20 of penetrating energy and a detector array 30. The carriage 12 includes a frame 16 supported by a plurality of wheels 14 and a pair of generally parallel and spaced apart arm members 18 extending downwardly from the sides of the frame 16. The arm members 18, and width of the frame 16, are spaced apart a distance equal to at least the diameter of the pipe 50 being analyzed so that the pipe 50 can be disposed between the arm members 18 when the carriage 12 engages the pipe 50. In such a position, the wheels 14 supporting the carriage 12 rest on the outer surface of the pipe, if not insulated, or otherwise on top of the insulation 52. The wheels 14 are oriented such that the carriage 12 can be rolled along the axial length of the pipe 50 as shown in FIG. 2.

Figure 10:
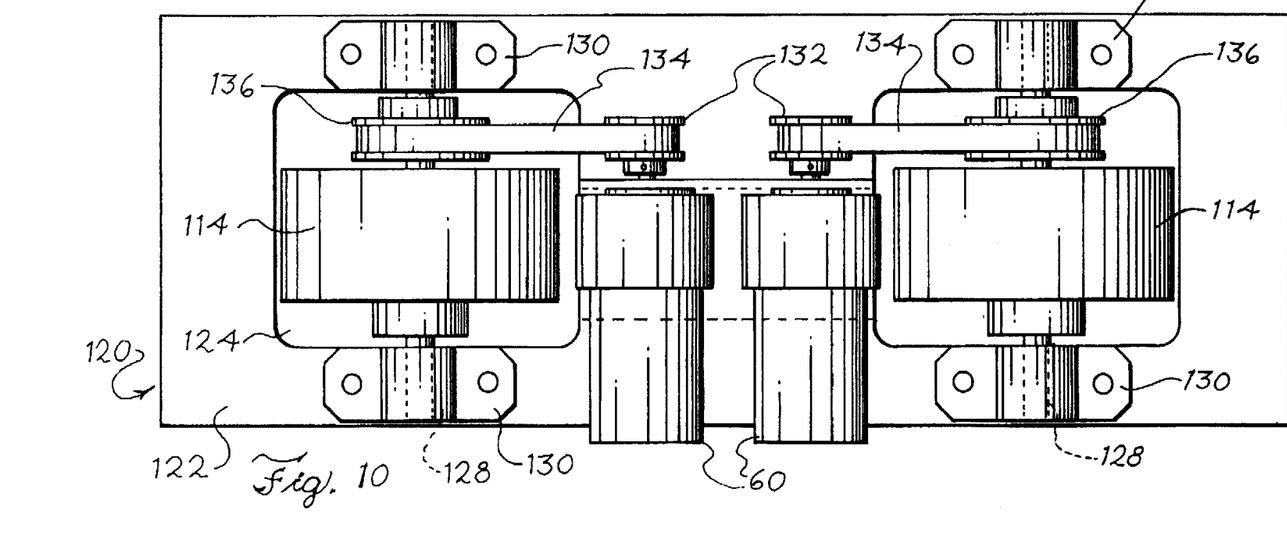
FIG. 10 is a top plan view of a drive assembly.
Figure 11:
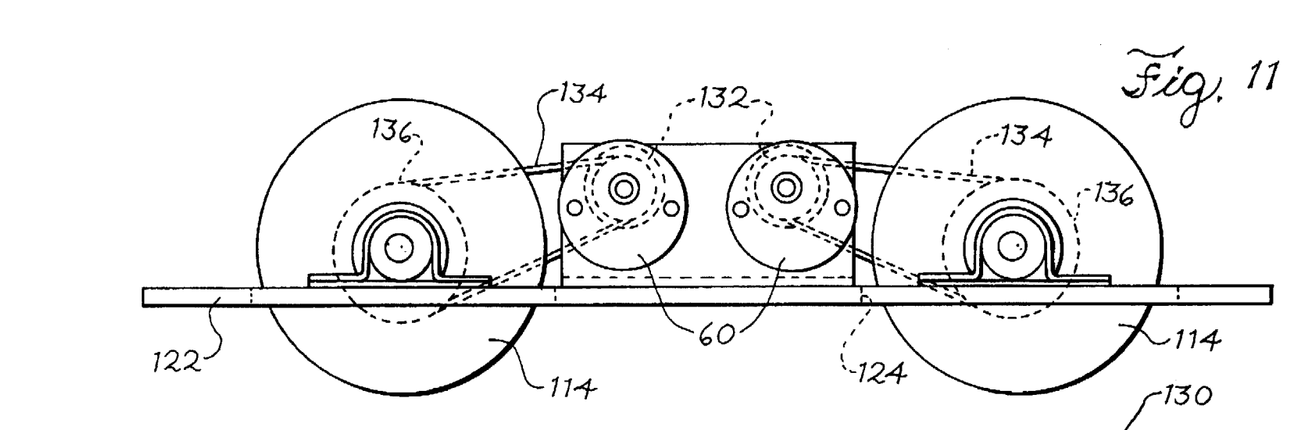
FIG. 11 is a side view of the drive assembly.
Figure 12:
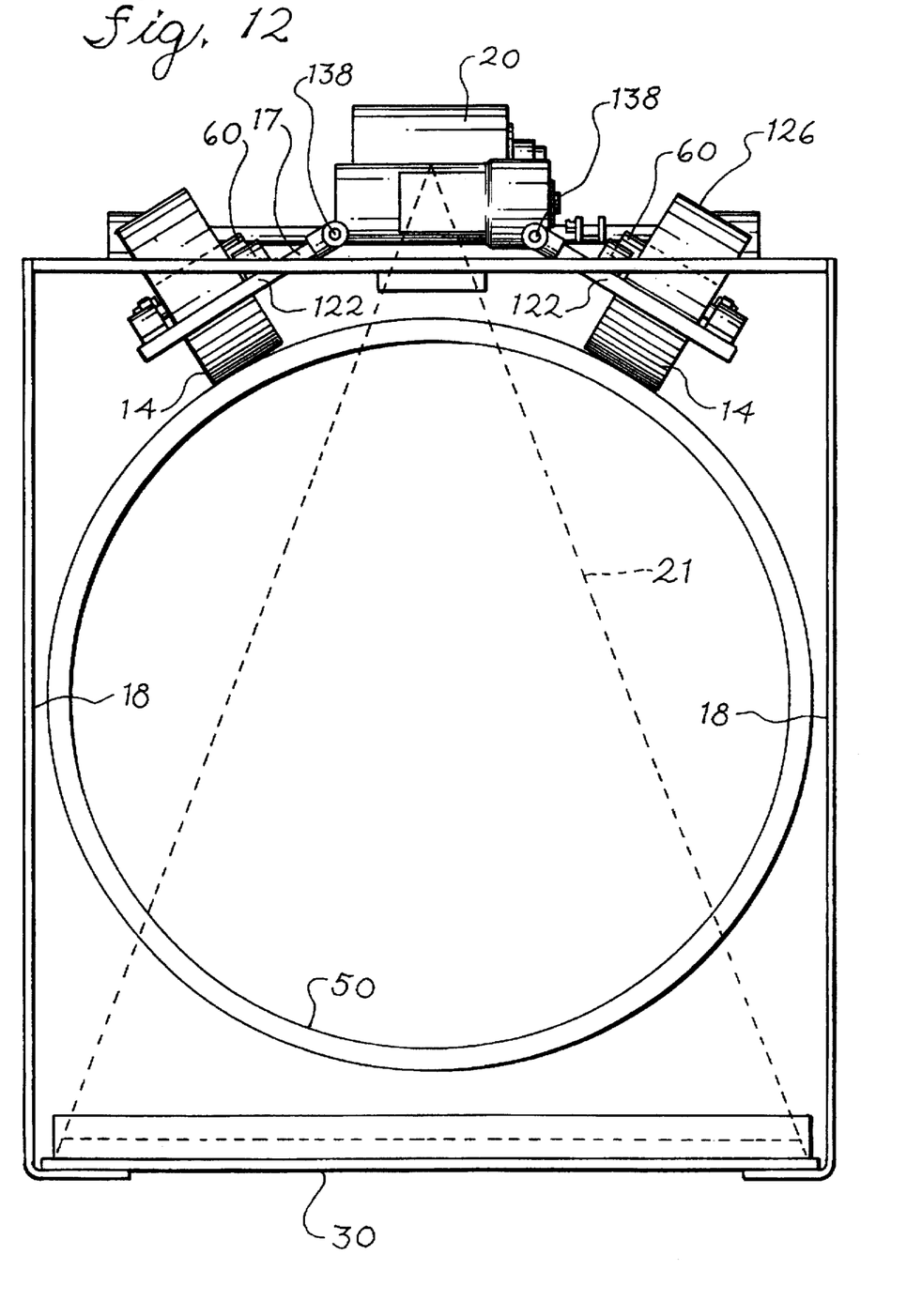
FIG. 12 is a front view of the apparatus having a pair of drive assemblies supported on a length of pipe.

In a preferred embodiment, shown in FIGS. 10–12, the carriage includes a pair of drive assemblies 120. The drive assemblies are pivotally attached to the carriage frame 126. Each drive assembly includes a pair of wheels 114 rotatably mounted to a support member 122. The wheels 114 are supported on an axle 128 which are mounted in brackets 130. The wheels 114 are disposed in and extend through an opening 124 in the support member. The wheels 114 have a relatively wide tread when compared with the diameter of the wheel and are therefore especially well adapted to grip the surface of the pipe wall or insulation. In operation, the drive assemblies 120 pivot about an axis 138 until the wheels are in full contact with pipe wall so that the tread of the wheels is approximately tangential to the surface of the pipe wall or insulation. Thus, the wheels on each assembly can more fully contact the pipe surface. This increases traction and improves the stability of the carriage as it moves along the length of pipe.

Figure 2:
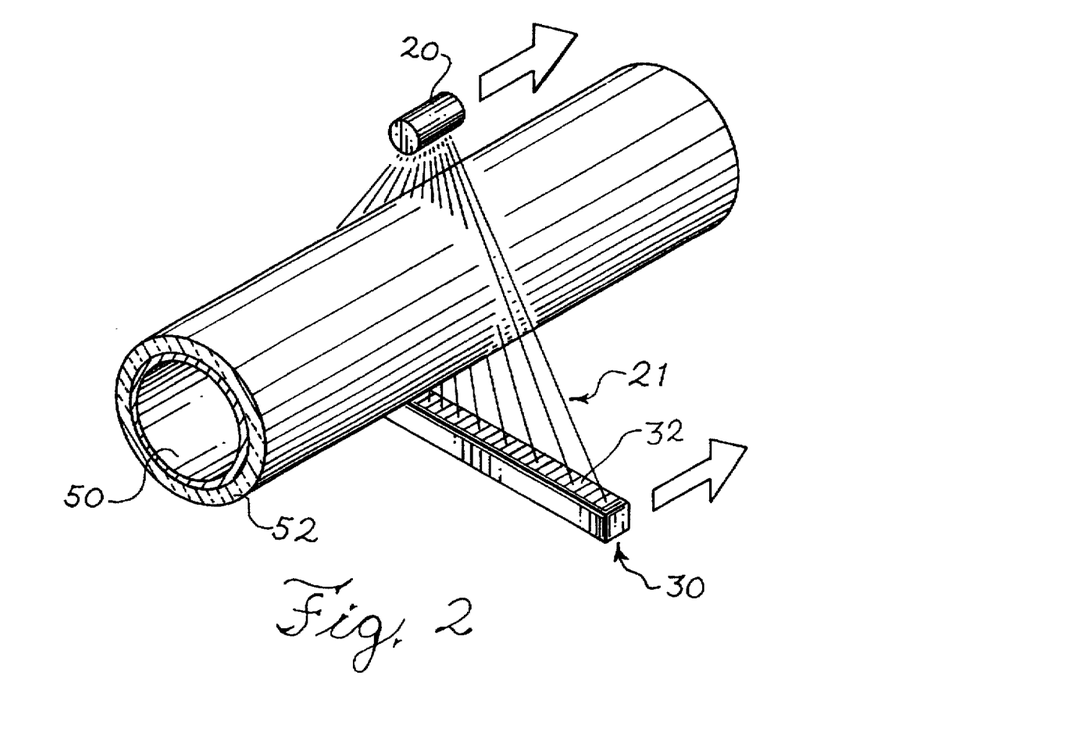
FIG. 2 is a pictorial of the source of penetrating energy and detector array moving along a length of pipe.
Figure 3:
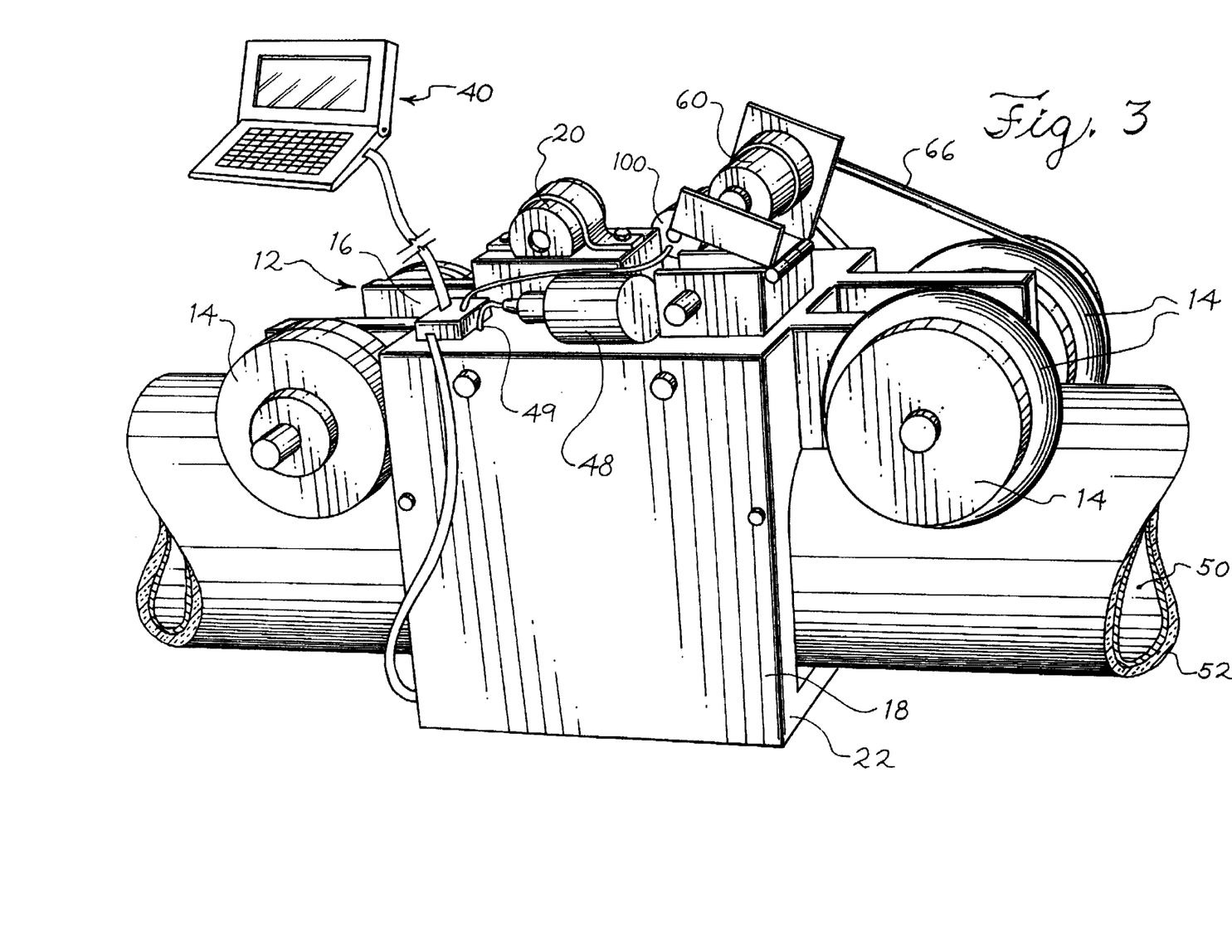
FIG. 3 is perspective view of the apparatus supported on a length of pipe.

Referring to the FIGS. 2–5, the source 20 of penetrating energy is preferably a gamma-ray source, although an x-ray source, or other suitable source, can also be used. In an exemplary embodiment, a low intensity Ir-192 gamma ray source was used. Referring to FIGS. 2 and 3, the source 20 is mounted to the carriage frame 16 and emits a fan-shaped beam 21 of penetrating gamma-rays directed downwardly through the pipe 50 disposed below it.

Figures 7, 8:
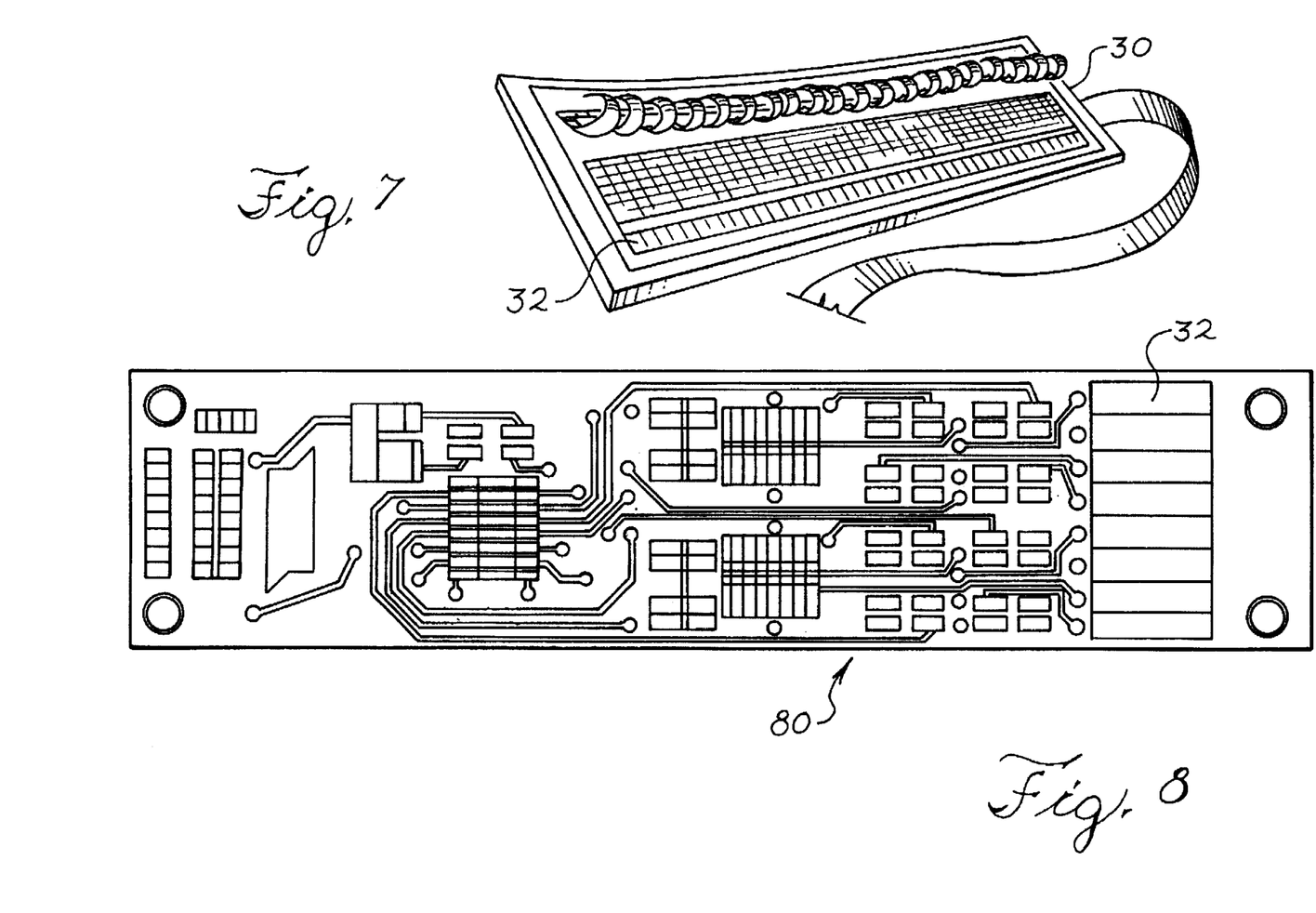
FIG. 7 is a perspective view of the detector array.
FIG. 8 is a top view of a detector module.

The detector array 30 is mounted between the spaced apart ends 22 of the arm members 18, and preferably has a length equal to or greater than the diameter of the pipe 50. For example, an array having a length equal to approximately twice the diameter of the pipe can receive a fan-shaped beam penetrating the entire diameter of the pipe. The detector array 30 is oriented so that its length is positioned generally perpendicular to the intended path of travel of the carriage 12, which is along the axial direction of the pipe 50. Referring to FIG. 7, the detector array 30 includes a plurality of individual detectors 32 arranged in an elongated array. In an exemplary embodiment, the array is linear and includes sixty-four (64) individual detectors. It should be understood that other configurations would work equally well, whereby the number of detectors depends on the diameter of the pipe and the amount of resolution desired when analyzing the pipe. Thus, the 64 detector array is meant to be illustrative, rather than limiting. In addition, the detectors, although depicted as linear array, can alternatively be arranged in an arcuate array configuration.

In a preferred embodiment, the detectors are $CdWO_4$/photodiode detectors. Each detector is about 0.13 inches long by 0.13 inches wide. Each detector includes a thick piece of $CdWO_4$ single crystal scintillator, which can detect the beam of energy penetrating the pipe, such as gamma-rays. Preferably, the thickness of the scintillator is such that it can detect more than 50% of the gamma rays emitted from a gamma-ray source, such as the Ir-192 source. An extremely low noise photodiode, preferably a Si photodiode, is provided to measure an optical signal generated by the scintillator upon reception of the gamma-rays. The photodiode produces a small current in response to the optical signal. An amplifier circuit is provided to amplify the signal from the photodiode. Thus, the output signal transmitted from each detector 32 is proportional to the intensity of the gamma-ray beam 21 received by the scintillator in that detector 32.

Referring to FIG. 7, the detectors 32 can be arranged in modules so as to allow for easy reconfiguration of smaller or larger arrays. In the exemplary modular arrangement shown in FIG. 7, eight detectors 32 are arranged to form an individual module, consisting of eight individual $CdWO_4$ crystals and eight photodiodes. Separate eight-detector modules 80 can then be placed side by side to form a larger array, for example the eight module, 64-detector array described above. An 8:1 multiplexer is provided in each module to multiplex the output from the eight detectors.

The 8:1 multiplexed analog signal from each detector module 80 is sent to a Data Acquisition System ("DAS") board, which also has an 8:1 multiplexer to further produce a 64:1 multiplexed analog signal. The DAS board is mounted on the carriage frame.

Figure 1:
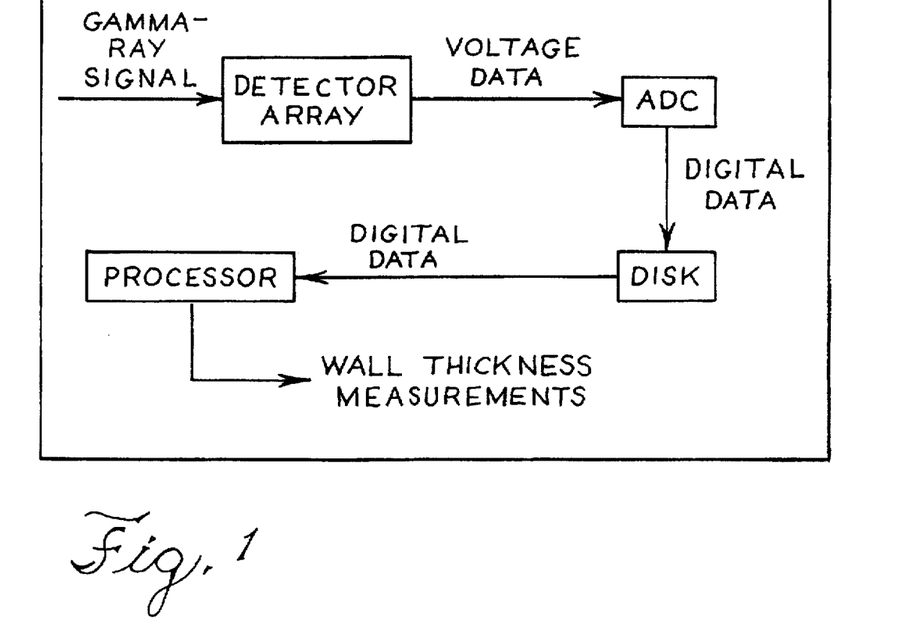
FIG. 1 is a schematic of the apparatus and method.

Referring to FIGS. 1 and 2, the apparatus 10 also includes a computer 40 which receives the analog signal from the DAS board. The computer 40 includes a analog-to-digital converter that converts the analog signal to a digital signal. The computer 40 employs logic to store and analyze the digital data and to compute the wall thickness of the pipe 50. The computer 40 can analyze the data and display the results on a CRT screen in real time as the apparatus 10 is propelled along the length of the pipe 50.

Figures 4, 5, 6:
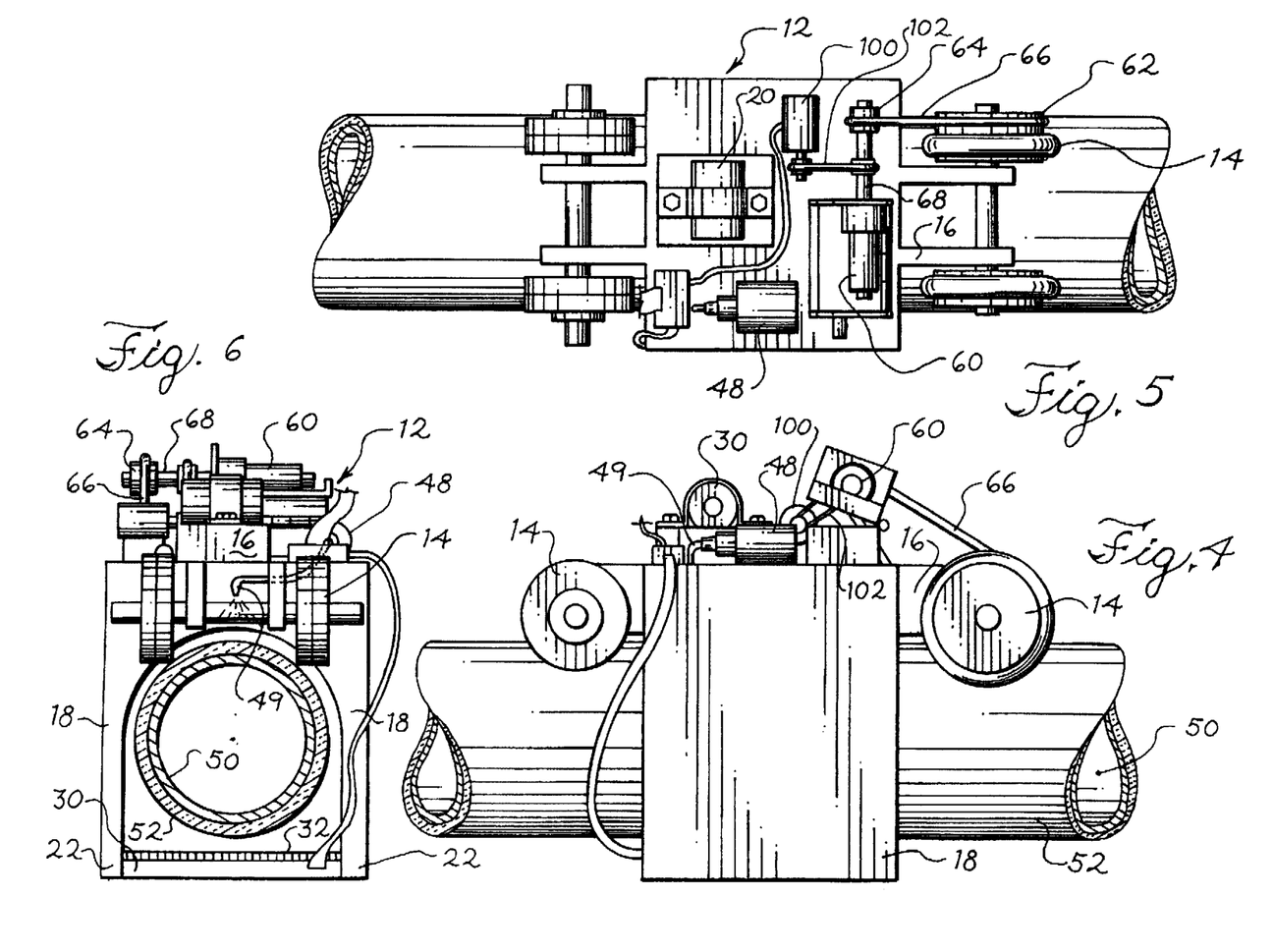
FIG. 4 is a side view of the apparatus supported by a pipe.
FIG. 5 is a top view of the apparatus supported by a pipe.
FIG. 6 is a front view of the apparatus supported by a pipe.

The computer 40 also can be provided with logic that activates a warning system when a recorded wall thickness value falls below a predetermined value entered into the computer 40. As shown in FIGS. 4–6, a marking device 46, consisting of a paint spraying system with a canister 48 and a nozzle 49, can be actuated by the computer to automatically mark the pipe 50 at the location where the below-minimum thickness value was recorded. It should be understood that other visual or audio warning signals, such as an alarm, would work equally well to notify the user about a particular section of pipe that merits closer scrutiny.

As shown in FIGS. 3–6, the apparatus 10 is provided with a low speed DC motor 60 mounted on the carriage 12. A pulley 62 is mounted co-axially with one of the wheels 14. A belt 66 connects the pulley 61 mounted on the wheel and second pulley 64 mounted on a drive shaft 68 extending from the motor 60. When powered, the motor 60 rotates the shaft which turns the pulley 64. The pulley 64 drives the belt 66 which then rotates the pulley 62 and attached wheels thereby propelling the carriage 12 along the pipe 50. It should be understood that other drive-train arrangements could be substituted for the belt and pulley arrangement, such as a chain and sprocket or a drive shaft and axle. Preferably, the motor 60 is variable speed and can be controlled remotely by a user. For example, a low voltage DC motor can propel the carriage along the length of the pipe at about a rate of 10 to 120 inches per minute. The speed and direction of the carriage is remotely controlled by varying the DC voltage to the motor.

Referring to the alternative embodiment shown in FIGS. 10–12, the drive assemblies 120 each preferably include a pair of DC motors 60 mounted on the support member 122. A pulley 132 is mounted on each motor and is connected with a belt 134 to a pulley 136 mounted on each axle 128. By using multiple motors, the size of the motors can be decreased and the overall size of the apparatus can be reduced. It should be understood that a single motor could also be installed on each drive assembly whereby it is connected to both wheels rotatably mounted on the support member.

In operation, as shown in FIGS. 3–6, the apparatus 10 is positioned on top of the pipe 50 so that the carriage wheels 14 are supported by the pipe 50, or insulation 52 on the pipe, and the arm members 18 extend downwardly on both sides of the pipe. It should be understood that the carriage can be configured to position the source on the side, bottom or any other part of the pipe, with the detector positioned opposite the source. Thus, the positioning of the apparatus on the top of the pipe is meant to be illustrative, rather than limiting.

The detector array 30 is secured to the ends 24 of the arm members 18 so that the diameter of the pipe and insulation is disposed between the source 20 mounted to the carriage frame 16 and the detector array 30. The source 20 is activated to emit a beam 21 of penetrating energy, or gamma-rays, that is directed at the detector array 30. The detectors 32 in the array receive the gamma-rays and measure the intensity of the beam 21 as it passes through the pipe 50. The user can employ the remote-control to activate the drive system and propel the carriage 12 along the length of the pipe 50. As the apparatus 10 moves along the pipe, data is collected from the detectors 32 at incremental time intervals, preferably from about 0.005 to 0.100 seconds. The distance between readings, i.e., the point at which data is collected, depends on the speed of the carriage and the rate of data collection. If the user desires a higher degree of resolution of a particular pipe section's wall thickness, the speed of the carriage can be slowed and the rate of data collection increased so as to provide more readings.

Alternatively, as shown in FIG. 5, the apparatus can include an encoder 100 mounted on the carriage and which is connected to the motor 60 with a belt 102. The encoder 100, which is connected to the computer 40, causes the computer to collect data at incremental distances along the length of the pipe as the motor rotates the wheels, rather than at incremental time intervals as described above. Alternatively, the encoder can be friction mounted on the top of the pipe. As the carriage runs along the length of the pipe, the encoder signals the computer to measure and record the intensity of the gamma rays received by the detectors in the array. In this way, the apparatus can be programmed to take readings at predetermined intervals along the length of the pipe, regardless of the speed of the carriage or motor.

The intensity of the beam 21 received by each detector 32 reflects the amount of gamma radiation absorbed as the beam 21 passes through the pipe across its diameter. Thus, the beam 21 penetrates two wall thicknesses: a first wall thickness located adjacent to the source and a second wall thickness located adjacent to the detector array. When there is a large defect or void in the wall of the pipe, more gamma rays are able to pass through the pipe and a corresponding higher intensity is registered at that detector. Thus, the measured intensity at each detector is directly correlated with the thickness of the pipe wall.

As discussed above, any insulation on the pipe can remain on the pipe while operating the apparatus. This is possible because the insulation absorbs only a relatively small number of gamma rays, regardless of its thickness, when compared with the adjacent pipe. Materials of higher density and higher atomic number absorb or attenuate a larger number of gamma rays than lower density materials. Insulation materials typically are made of lighter density and lower atomic number components than the pipe, which typically is made of steel, i.e., a higher density and higher atomic number material. Thus, the intensity level registered by the detectors does not increase a measurable amount even if a large void or defect is present in the insulation. In contrast, a very small void in a steel pipe will be represented by a large intensity change registered at the same detectors. Thus, the insulation does not measurably affect the measured intensity and corresponding thickness computations.

In addition, voids and defects in the insulation material are generally larger in area and more gradual or tapered in nature than the typical defects found in the wall of the pipe. Thus, the gamma ray attenuation due to defects in the insulation changes more slowly when compared to the attenuation due to defects in the wall of the pipe. This difference in the rate of change can be analyzed by the computer to distinguish further between defects found in the insulation and in the pipe wall.

The present invention provides significant advantages over the prior art methods. Importantly, the apparatus can be programmed to measure the thickness of the pipe walls continuously along the length of the pipe. Different system resolution can be achieved by controlling the speed of the carriage and the intervals between measurements. In addition, substantially the entire width of the pipe can be analyzed in a single pass by employing an elongated array of detectors, rather than a single detector, which collects data for only a narrow discrete path defined by the width of the detector. Local defects, which may not be detected by a single detector due to its size limitations, can be detected and recorded.

Once the data is collected by the computer, it can be used to calculate the thickness of the pipe wall and can be displayed by the user in various forms. For example, the thickness of the wall can be displayed numerically, plotted as a graph, or displayed as a radiograph image. In addition, the data collected by each detector can be viewed independently or in combination with other detectors. Moreover, since the data is digitally stored, and can be transferred to data disks, measurements which were made days, months, or even years before can be compared quickly and easily. Thus, the data can be analyzed to evaluate the deterioration of the pipe over time. Alternatively, the data can be analyzed and displayed in real time as the apparatus moves along the length of the pipe so as to provide the user with immediate feedback on the wall thickness of the pipe.

Before taking measurements, the apparatus preferably is calibrated. To calibrate the system, the apparatus is placed on a section of pipe and a reading is taken by each detector in the detector array, with gamma rays being emitted by the source and received by the detectors. A known thickness of metal of the same type used in the pipe then is inserted between the source and array and another reading is taken for the entire array. This step is repeated several times, each time inserting different but known thicknesses of metal while measuring the intensity of the gamma rays received at each detector in the array. The computer is programmed to make a polynomial fit of the data for each detector as a function of the metal thickness. Thus, the computer calibrates the system whereby the signal received at each detector is correlated with a known thickness. During the actual scanning of the pipe, the computer can then calculate the actual thickness of the pipe wall based on the measured intensity of the beam received at the detectors in the array.

Figure 9:
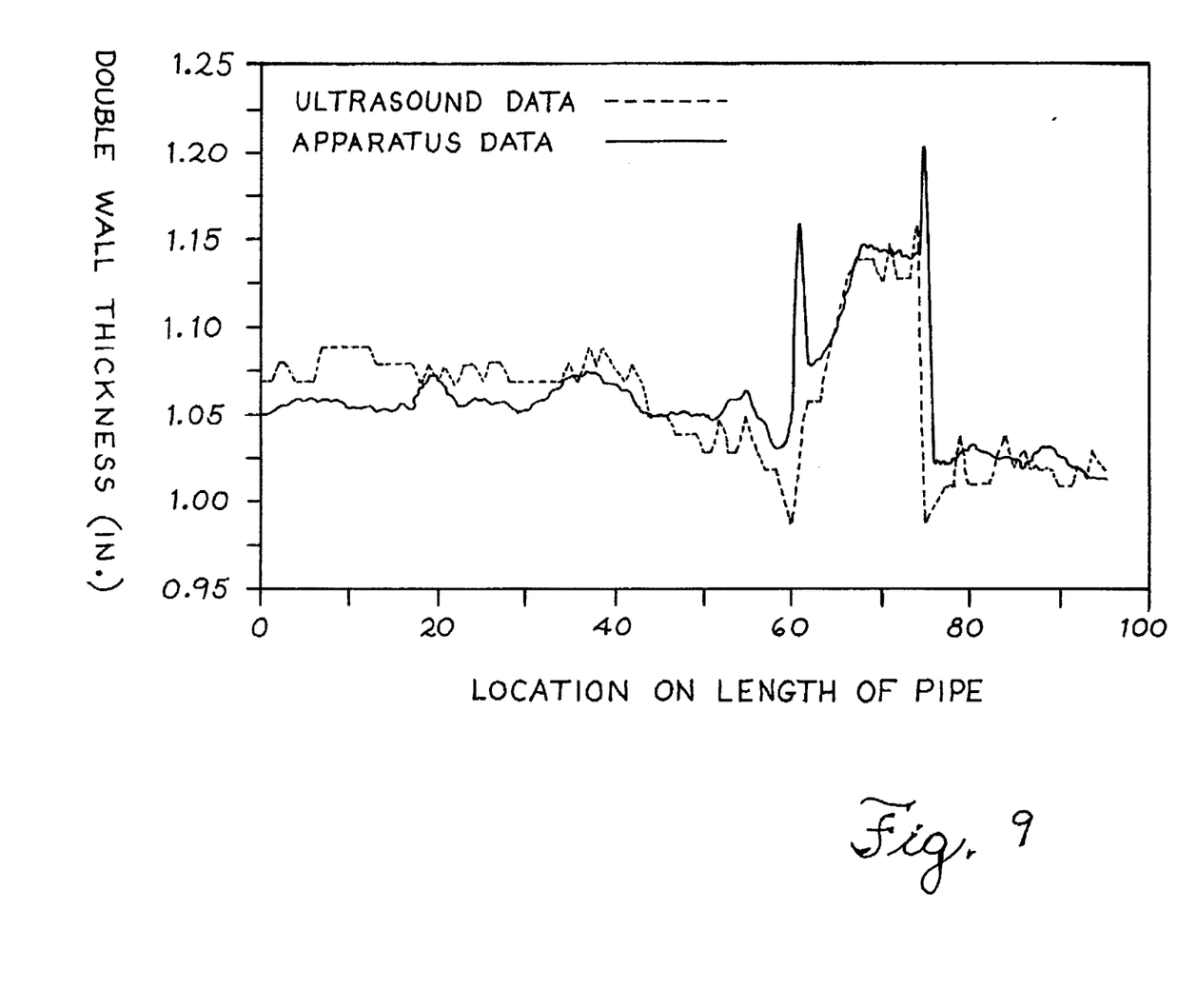
FIG. 9 is a graph of wall thicknesses measured by the apparatus compared with wall thicknesses measured by ultrasound.

The improved resolution and accuracy of the thickness measurements has been proven in actual testing by comparing readings taken from the apparatus with readings recorded using the conventional ultrasonic method. In particular, FIG. 9 shows the results of wall-thickness measurements taken by the ultrasonic method compared with wall-thickness measurements taken by the apparatus along an eight foot section of insulated pipe having a 4 inch diameter. The recorded wall-thickness measurements indicate that a new section of pipe, about 14 inches long and having a greater wall thickness than the adjacent sections of pipe, was positioned in the length of pipe between the 60 inch and 74 inch location along the length of the pipe, as shown in FIG. 9. The spikes, or increased thickness measurements at approximately the 60 inch and 74 inch mark indicate the presence of welds securing the new section of pipe to the adjacent sections of pipe.

Referring to Tables I and II, the results of tests performed on two twelve-inch sections of the eight foot pipe are shown. The ultrasound tests were performed on opposite sides of the pipe and the results were added to provide a double-thickness measurement of the pipe for comparison with the double-wall reading of the apparatus. The ultrasound readings were taken every one inch along the section of pipe, with the ultrasound device having a 1"×1" cross-section. Correspondingly, the apparatus recorded measurements every 0.021 inches.

In order to provide comparable data, the data from each detector was averaged for the 47 readings taken along the one inch path. Similarly, the data from the array was averaged along the diameter of the pipe so as to correspond with the reading of the one inch ultrasonic pattern.

wide variation between the maximum and minimum values within the grid, while the ultrasound data does not show any variations at all. Moreover, the system is not limited to a 1"×1" grid. Instead, it is capable of measuring substantially the entire width of the pipe, rather than the narrow discrete area of the ultrasound or single detector systems. In addition, the apparatus completed the measuring of the pipe in fraction of the time required to perform the ultrasound testing.

Thus, the present invention provides significant advantages over other devices and methods for inspecting and measuring pipe wall thicknesses. The apparatus allows a user to measure the wall thickness of an entire length of pipe in a single pass, without having to stop and record measurements at discrete intervals. Thus, the invention provides an extremely fast and accurate device and method for assessing the integrity of the pipeline. In addition, by providing an array of detectors, substantially the entire width of the pipe can be evaluated during a single pass, rather than a narrow, discrete path defined by a single detector. Moreover, the output of the detectors can be displayed in a variety of ways, including a radiograph image of the pipe wall. Thus, less passes have to be made, and the costs of inspection are greatly reduced. In addition, the remote-controlled carriage allows the user to place themselves at a distance from the section of pipe being analyzed, thereby removing themselves from a potentially dangerous situation such as where the pipe carries hazardous materials and leakage or failure is imminent. Also, the carriage provides a unique way to inspect and measure the wall thickness of a length of pipe installed in a pipeline in that it can be propelled along the length of the pipe rather than moving the pipe relative to the source and detector array.

Although the present invention has been described with reference to preferred embodiments, those skilled in the art

TABLE I

| ULTRASOUND THICKNESS MEASUREMENTS (PIPE SECTION 1) | | | | | | | | | | | |
|---|---|---|---|---|---|---|---|---|---|---|---|
| .99 | 1.03 | 1.06 | 1.06 | 1.08 | 1.1 | 1.13 | 1.14 | 1.14 | 1.14 | 1.13 | 1.15 |
| APPARATUS THICKNESS MEASUREMENTS (PIPE SECTION 1) | | | | | | | | | | | |
| MEAN THICKNESS | | | | | | | | | | | |
| 1.047 | 1.163 | 1.079 | 1.083 | 1.09 | 1.101 | 1.123 | 1.141 | 1.149 | 1.148 | 1.145 | 1.143 |
| STANDARD DEVIATION | | | | | | | | | | | |
| 0.054 | 0.044 | 0.047 | 0.043 | 0.039 | 0.036 | 0.036 | 0.04 | 0.04 | 0.042 | 0.041 | 0.043 |
| MAXIMUM VALUE | | | | | | | | | | | |
| 1.246 | 1.309 | 1.223 | 1.216 | 1.222 | 1.26 | 1.235 | 1.252 | 1.261 | 1.253 | 1.254 | 1.258 |
| MINIMUM VALUE | | | | | | | | | | | |
| 0.94 | 1.049 | 0.974 | 0.991 | 0.999 | 1 | 1.027 | 1.018 | 1.064 | 1.014 | 1.047 | 0.995 |

TABLE II

| ULTRASOUND THICKNESS MEASUREMENTS (PIPE SECTION 2) | | | | | | | | | | | |
|---|---|---|---|---|---|---|---|---|---|---|---|
| 1.13 | 1.13 | 1.16 | 0.99 | 1 | 1.01 | 1.01 | 1.04 | 1.01 | 1.01 | 1.01 | 1.02 |
| APPARATUS THICKNESS MEASUREMENTS (PIPE SECTION 2) | | | | | | | | | | | |
| MEAN THICKNESS | | | | | | | | | | | |
| 1.145 | 1.142 | 1.133 | 1.202 | 1.025 | 1.023 | 1.022 | 1.028 | 1.035 | 1.033 | 1.029 | 1.025 |
| STANDARD DEVIATION | | | | | | | | | | | |
| 0.044 | 0.044 | 0.045 | 0.08 | 0.037 | 0.04 | 0.042 | 0.042 | 0.039 | 0.034 | 0.032 | 0.031 |
| MAXIMUM VALUE | | | | | | | | | | | |
| 1.269 | 1.263 | 1.249 | 1.366 | 1.18 | 1.164 | 1.167 | 1.171 | 1.173 | 1.142 | 1.155 | 1.127 |
| MINIMUM VALUE | | | | | | | | | | | |
| 1.004 | 1 | 0.986 | 1.003 | 0.939 | 0.94 | 0.934 | 0.925 | 0.935 | 0.957 | 0.952 | 0.958 |

In viewing the results of these tests, it is clear that there is a remarkable correlation between the measurements, although the apparatus provides significantly better accuracy. For example, as shown in TABLES I and II, the measurements recorded by the apparatus clearly show a will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

I claim:

1. An apparatus adapted for inspecting and measuring the wall thickness of a length of pipe, said apparatus comprising:
   a carriage adapted to be movably mounted on said length of pipe;
   a source emitting a beam of penetrating energy mounted on said carriage;
   a detector array having a plurality of detectors arranged in an elongated array to receive and measure the intensity of said beam of penetrating energy, said detector array mounted on said carriage in a spaced apart relationship with said source so as to allow the diameter of the pipe to pass between them as the carriage is moved axially along its length, said detector array oriented so that its length is positioned generally perpendicular to the intended path of travel of the carriage along the pipe.

2. The apparatus of claim 1 wherein said carriage is adapted to be supported by and propelled along the length of the pipe.

3. The apparatus of claim 2 wherein said carriage is adapted to be propelled along said length of pipe at a rate of from about 10 inches per minute to about 120 inches per minute.

4. The apparatus of claim 1 further comprising a computer connected to receive and store output from said detector array measuring the intensity of said beam of penetrating energy.

5. The apparatus of claim 4 further comprising an encoder mounted on said carriage, said encoder signaling said computer to collect data from said detector array at predetermined intervals along the length of pipe.

6. The apparatus of claim 4 wherein said computer is connected to receive an analog signal from said detector array and convert said signal to a digital signal, said computer comprising logic to store and analyze said digital signal so as to compute the wall thickness of said pipe.

7. The apparatus of claim 6 wherein said computer is programmed to analyze the output from said detectors and compute the wall thickness in real time.

8. The apparatus of claim 6 wherein data is collected from said detector array from about 0.005 to about 0.100 second time intervals.

9. The apparatus of claim 6 including means for providing notice when said computed wall thickness falls below a predetermined minimum value.

10. The apparatus of claim 9 including means for marking said pipe when said computed wall thickness falls below said predetermined minimum value.

11. The apparatus of claim 1 wherein said source of penetrating energy comprises a gamma-ray source.

12. The apparatus of claim 11 wherein said source is a low intensity Ir-192 gamma-ray source.

13. The apparatus of claim 11 wherein said detector array comprises a plurality of $CdWO_4$/photodiode detectors, wherein a $CdWO_4$ scintillator is adapted to detect said gamma rays and wherein said photodiode is adapted to measure an optical signal generated by said $CdWO_4$ scintillator.

14. The apparatus of claim 13 wherein each of said detectors further comprises an amplifier circuit adapted to amplify a current signal generated by said photodiode.

15. The apparatus of claim 1 wherein said carriage further comprises a plurality of wheels adapted to engage said pipe, whereby said carriage can be rolled along the length of pipe.

16. The apparatus of claim 15 wherein said carriage is self-propelled.

17. The apparatus of claim 16 wherein said carriage further comprises a DC motor operably connected to at least one of said wheels to propel said apparatus along said length of pipe.

18. The apparatus of claim 17 wherein said carriage is remote controlled.

19. The apparatus of claim 15 wherein said carriage further comprises a frame supported by said wheels, said source mounted to said frame, and a pair of spaced apart and generally parallel arm members extending downwardly from said frame, said arm members mounted to and supporting opposite ends of said detector array.

20. The apparatus of claim 19 wherein said carriage further comprises at least one drive device connected to said frame, said at least one drive device including a support member, wherein at least one of said wheels is rotatably mounted to said support member.

21. The apparatus of claim 20 wherein said at least one drive device includes at least one motor mounted on said support member, said motor operably connected to at least one of said wheels to propel the carriage along the length of pipe.

22. An apparatus adapted for inspecting and measuring the wall thickness of a length of pipe, said apparatus comprising:
   a carriage adapted to be movably supported by said length of pipe, said carriage comprising a plurality of wheels adapted to engage said pipe;
   a source emitting a beam of penetrating energy mounted on said carriage;
   a detector array having a plurality of detectors arranged in an elongated array to receive and measure the intensity of said beam of penetrating energy, said detector array mounted on said carriage in a spaced apart relationship with said source so as to allow the diameter of the pipe to pass between them as the carriage is propelled axially along its length, said detector array oriented so that its length is positioned generally perpendicular to the carriage's intended path of travel along the pipe; and
   a computer connected to receive and store output from said detector array measuring the intensity of said beam of penetrating energy, said computer comprising logic to store and analyze said output so as to compute the wall thickness of said pipe.

23. The apparatus of claim 22 wherein said carriage is self-propelled and remote-controlled.

24. A method for inspecting and measuring the wall thickness of a pipe, said method comprising:
   providing an apparatus for measuring the wall thickness of said pipe, said apparatus comprising a carriage supported on said pipe, a source adapted to emit a beam of penetrating energy mounted on said carriage, a detector array having a plurality of detectors arranged in an elongated array adapted to receive and measure the intensity of said beam of penetrating energy emitted from said source, said detector array mounted to said carriage in a spaced apart relationship with said source;
   positioning said apparatus on said pipe so that said carriage is supported by the pipe and so that the diameter of the pipe is disposed between said detector array and said source, said detector array oriented so that its length is positioned generally perpendicular to the length of said pipe;

propelling said apparatus along the axial direction of said length of said pipe;

emitting a beam of energy from said source;

receiving said beam of energy at said detector array;

collecting output measuring the intensity of the beam from each of said detectors in said array;

computing the wall thickness of said pipe from the output collected from the detectors as said apparatus is propelled along the length of pipe.

25. The method of claim 24 wherein said pipe is insulated.

26. The method of claim 24 wherein the step of propelling said apparatus comprises propelling said carriage along the length of pipe at a rate of from about 10 inches per minute to about 120 inches per minute.

27. The method of claim 24 wherein said step of collecting comprises collecting said output from said detector array from about 0.005 to about 0.010 second time intervals.

28. The method of claim 24 further comprising a motor for propelling the apparatus along the axial direction of the pipe and an encoder mounted on said carriage, said encoder signaling said computer to collect data from said detector array at predetermined intervals along the length of pipe.

29. The method of claim 28 further comprising the step of displaying said computed wall thickness in real time.

30. The method of claim 24 wherein said step of collecting comprises collecting data with a computer that receives and stores the output from said detector array.

31. The method of claim 30 wherein said computer is adapted to receive an analog signal from said detector array and convert said signal to a digital signal, said computer comprising logic to store and analyze said digital signal so as to compute the wall thickness of said pipe.

32. The method of claim 31 further comprising the step of providing notice when said computed wall thickness falls below a predetermined minimum value.

33. The method of claim 32 wherein the step of providing notice comprises marking said pipe when said computed wall thickness falls below said predetermined minimum value.

34. The method of claim 24 wherein said source of penetrating energy comprises a gamma-ray source.

35. The method of claim 34 wherein said source is a low intensity Ir-192 gamma-ray source.

36. The method of claim 34 wherein said detector array comprises a plurality of $CdWO_4$/photodiode detectors, wherein a $CdWO_4$ scintillator is adapted to detect said gamma rays and wherein said photodiode is adapted to measure an optical signal generated by said $CdWO_4$ scintillator.

37. The method of claim 36 wherein each of said detectors further comprises an amplifier circuit adapted to amplify a current signal generated by said photodiode.

38. The method of claim 24 wherein said carriage further comprises a plurality of wheels adapted to engage said pipe, and wherein said step of propelling said apparatus comprises rolling said carriage along the length of said pipe.

39. The method of claim 38 wherein said carriage is self-propelled.

40. The method of claim 39 wherein said carriage further comprises a DC motor operably connected to at least one of said wheels to propel said carriage along said length of said pipe.

41. The method of claim 39 wherein said carriage is remote controlled.

42. The method of claim 38 wherein said carriage further comprises a frame supported by said wheels, said source mounted to said frame, and a pair of spaced apart and generally parallel arm members extending downwardly from said frame, said arm members mounted to and supporting opposite ends of said detector array.

43. The method of claim 42 wherein said carriage further comprises at least one drive device connected to said frame, said at least one drive device including a support member and a motor mounted on said support member, wherein at least one of said wheels is rotatably mounted to said support member and said motor is operably connected to at least one of said wheels to propel the carriage along the length of pipe.

44. The method of claim 24 further comprising the step of calibrating each of said detectors.

45. The method of claim 44 where said step of calibrating comprises measuring the intensity of the beam as it passes through various known thicknesses of metal and programming the computer to compute the thickness of the pipe wall corresponding to the measured intensity of the beam as it passes through the known thicknesses of metal.

* * * * *